United States Patent [19]

Nakane et al.

[11] 4,418,076
[45] Nov. 29, 1983

[54] 7-OXABICYCLOHEPTANE HYDRAZONE PROSTAGLANDIN ANALOGS USEFUL IN TREATING THROMBOLYTIC DISEASES

[75] Inventors: Masami Nakane, Plainsboro; Joyce Reid, Dayton; Martin F. Haslanger, Lambertville, all of N.J.

[73] Assignee: E. R. Squibb & Sons, Inc., Princeton, N.J.

[21] Appl. No.: 374,125

[22] Filed: May 3, 1982

[51] Int. Cl.³ ................... A61K 31/34; C07D 307/00
[52] U.S. Cl. .................................. 424/285; 542/420; 542/418; 549/463
[58] Field of Search ............... 549/463; 542/418, 420; 424/285

[56] References Cited

U.S. PATENT DOCUMENTS

| | | | |
|---|---|---|---|
| 4,143,054 | 3/1979 | Sprague | 549/463 |
| 4,187,236 | 2/1980 | Sprague | 549/463 |
| 4,220,594 | 9/1980 | Sprague | 549/459 |
| 4,228,180 | 10/1980 | Sprague | 549/463 |
| 4,254,044 | 3/1981 | Sprague | 549/463 |

FOREIGN PATENT DOCUMENTS 43292 6/1982 European Pat. Off. .
2039909 8/1980 United Kingdom .

*Primary Examiner*—Henry R. Jiles
*Assistant Examiner*—Bernard Dentz
*Attorney, Agent, or Firm*—Lawrence S. Levinson; Burton Rodney

[57] ABSTRACT

7-Oxabicycloheptane hydrazone prostaglandin analogs are provided having the structural formula

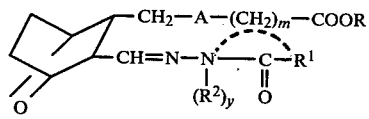

and including all stereoisomers thereof. pa The compounds are cardiovascular agents useful, for example, in the treatment of thrombolytic disease.

13 Claims, No Drawings

7-OXABICYCLOHEPTANE HYDRAZONE PROSTAGLANDIN ANALOGS USEFUL IN TREATING THROMBOLYTIC DISEASES

DESCRIPTION OF THE INVENTION

The present invention relates to 7-oxabicycloheptane hydrazone prostaglandin analogs which are cardiovascular agents useful, for example, in the treatment of thrombolytic disease. These compounds have the structural formula

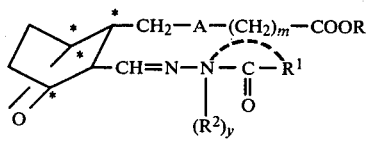

and including all stereoisomers thereof, wherein
A is CH=CH or $(CH_2)_2$; m is 1 to 8; y is 0 or 1;
R is H or lower alkyl; where y is 1, $R^2$ is H or lower alkyl; and
$R^1$ is lower alkyl, lower alkoxy, aryl, alkylamino, arylamino, aryloxy, pyridinyl or cycloalkyl or where y is 0 as indicated by

$R^1$ can be a $-(CH_2)_x-$ linking group (wherein x is 3, 4 or 5) which together with

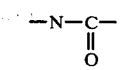

may form an N-containing 5-, 6- or 7-membered heterocycle, with the proviso that when $R^2$ is H, $R^1$ is lower alkoxy.

The term "lower alkyl" or "alkyl" as employed herein includes both straight and branched chain radicals of up to 12 carbons, preferably 1 to 8 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including a halo-substituent, such as F, Br, Cl or I or $CF_3$, an alkoxy substituent, an aryl substituent, an alkyl-aryl substituent, a haloaryl substituent, a cycloalkyl substituent or an alkylcycloalkyl substituent.

The term "cycloalkyl" includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with 1 or 2 halogens, 1 or 2 lower alkyl groups and/or lower alkoxy groups.

The term "aryl" or "Ar" as employed herein refers to monocyclic or bicyclic aromatic groups containing from 6 to 10 carbons in the ring portion, such as phenyl, naphthyl, substituted phenyl or substituted naphthyl wherein the substituent on either the phenyl or naphthyl may be lower alkyl, halogen (Cl, Br or F), or lower alkoxy.

The term "lower alkoxy", "alkoxy" or "aryloxy" includes any of the above lower alkyl or alkyl groups or aryl groups linked to an oxygen atom.

The term "halogen" or "halo" as used herein refers to chlorine, bromine, fluorine or iodine with fluorine being preferred.

The terms "$(CH_2)_m$" and "$(CH_2)_x$" include a straight or branched chain radical having from 1 to 8 carbons in the normal chain in the case of "$(CH_2)_m$" and from 3 to 5 carbons in the normal chain in the case of "$(CH_2)_x$" and may contain one or more lower alkyl substituents. Examples of $(CH_2)_m$ and $(CH_2)_x$ groups include $CH_2$, $CH_2CH_2$, $(CH_2)_3$, $(CH_2)CH_4$, $(CH_2)_5$, $(CH_2)_6$, $(CH_2)_7$,

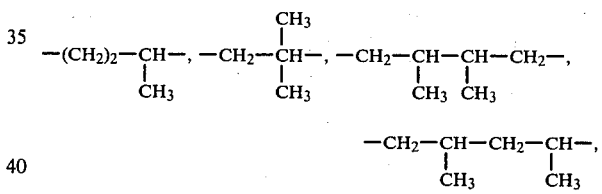

and the like.

Preferred are those compounds of formula I wherein A is CH=CH, m is 2 to 4, y is 1, R is H or lower alkyl, and $R^1$ is propyloxy or butyloxy and $R_2$ is H.

The various compounds of the invention may be prepared as outlined below.

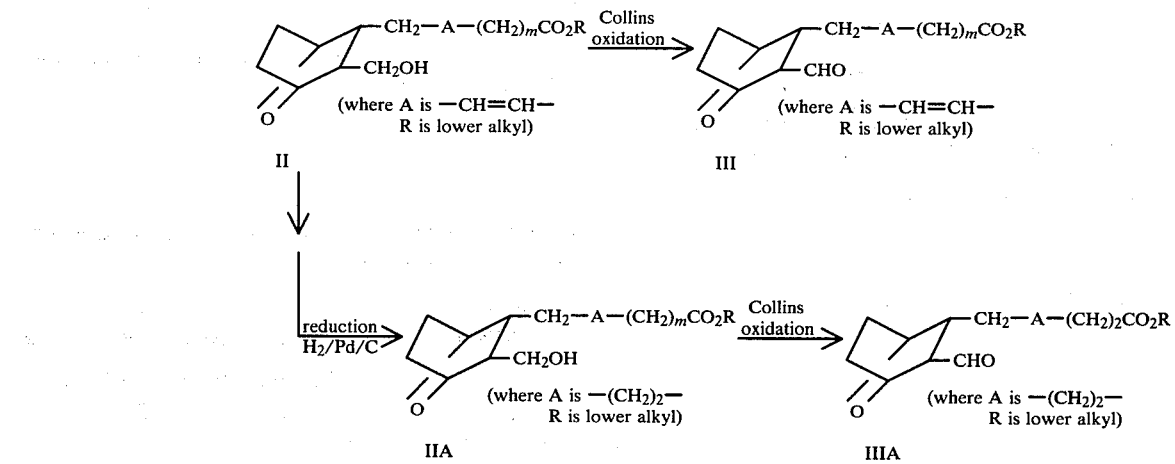

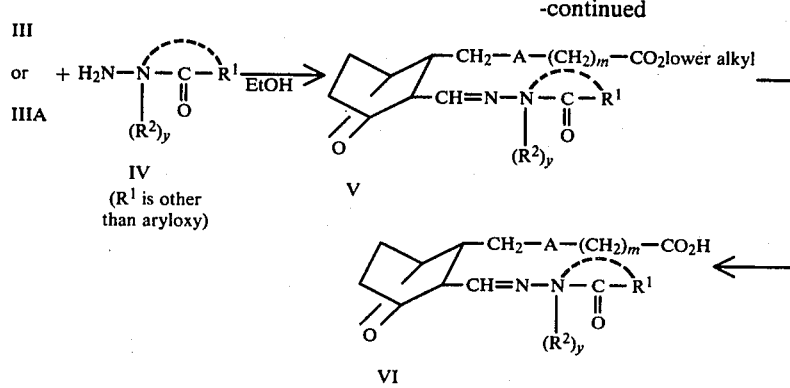

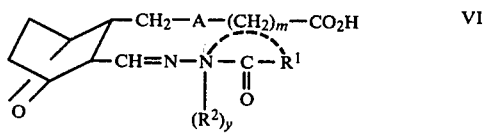

The starting lower alkyl ester containing the hydroxymethyl group (that is, compound II) (prepared as described in U.S. Pat. No. 4,143,054) is used to form the aldehyde III (where A is —CH=CH—) or IIIA (where A is —($CH_2$)$_2$—). Thus, to form aldehyde III where A is —CH=CH—, compound II is subjected to a Collins oxidation, for example, by reacting II with chromium trioxide in pyridine. To form the aldehyde III (where A is ($CH_2$)$_2$), compound II is reduced, for example with hydrogen over a palladium on carbon catalyst, to form hydroxymethyl compound IIA (where A is ($CH_2$)$_2$) and compound IIA is subjected to a Collins oxidation to form aldehyde IIIA (where A is ($CH_2$)$_2$).

Aldehyde III or IIIA of the structure

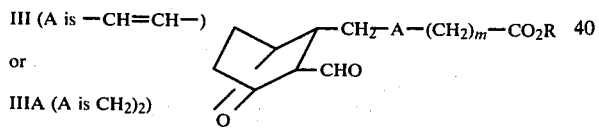

wherein R is lower alkyl is reacted with a hydrazine derivative, such as of the structure

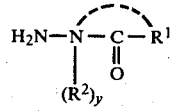

employing a molar ratio of III or IIIA:IV of within the range of from about 0.8:1 to about 1:1, in the presence of a solvent, such as methanol or ethanol, to form an ester compound of the structure

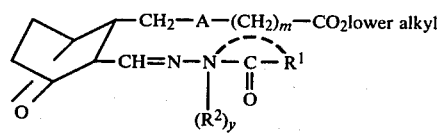

(where A is ($CH_2$)$_2$ or —CH=CH—).

The ester V can be converted to the free acid, that is, to

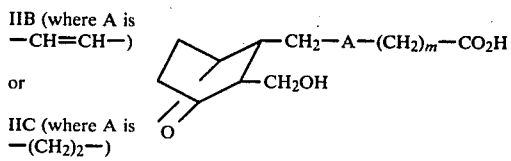

by treating the ester V with a base, such as lithium hydroxide, followed by neutralization with an acid, such as dilute hydrochloric acid or oxalic acid.

Where $R^1$ is aryloxy, the esters II or IIA are first converted to the corresponding acid, for example, by reaction with a strong base, such as sodium hydroxide

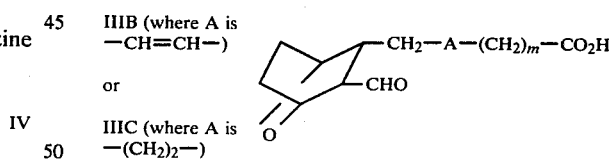

The acid IIB or IIC may then be subjected to a Collins oxidation as described hereinbefore to form the aldehyde IIIB or IIIC

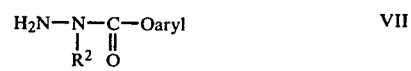

The aldehyde IIIB or IIIC may then be reacted with an arylcarbazate $$H_2N-\underset{R^2}{\underset{|}{N}}-\underset{O}{\underset{\|}{C}}-Oaryl \qquad VII$$

as described hereinbefore to form the corresponding compound of the invention

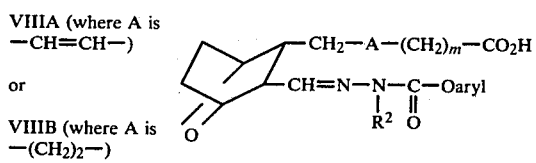

The compounds of this invention have four centers of asymmetry as indicated by the asterisks in formula I. However, it will be apparent that each of the formulae set out above which do not include asterisks still represent all of the possible stereoisomers thereof. All of the various stereoisomeric forms are within the scope of the invention.

The various stereoisomeric forms of the compounds of the invention, namely, cis exo, cis endo and all trans forms and stereoisomeric pairs may be prepared as shown in the working Examples which follow and by employing starting materials and following the procedures as outlined in U.S. Pat. No. 4,143,054. Examples of such stereoisomers are set out below.

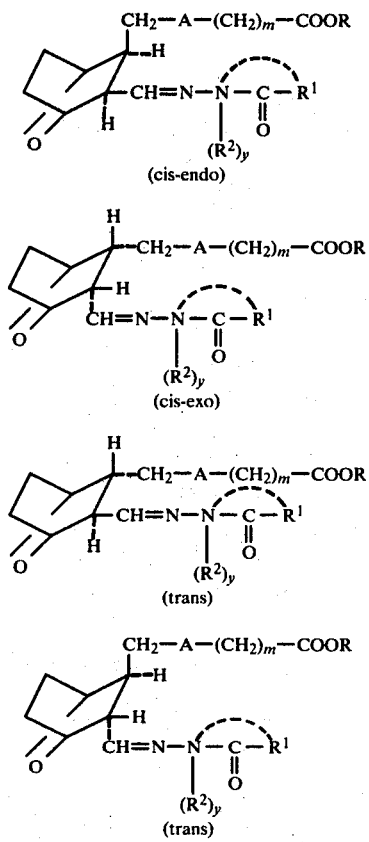

The nucleus in each of the compounds of the invention is depicted as

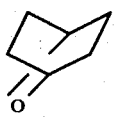

for matter of convenience; it will also be appreciated that the nucleus in the compounds of the invention may be depicted as

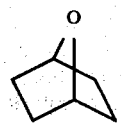

The compounds of this invention are cardiovascular agents useful as platelet aggregation inhibitors, e.g., for treatment of thrombolytic disease, such as coronary or cerebral thromboses. They are also selective thromboxane $A_2$ receptor antagonist and synthetase inhibitors, e.g., having a vasodilatory effect for treatment of myocardial ischemic disease, such as angina pectoris. They can be administered orally or parenterally to various mammalian species known to be subject to such maladies, e.g., cats, dogs, and the like in an effective amount within the dosage range of about 1 to 100 mg/kg, preferably about 1 to 50 mg/kg and especially about 2 to 25 mg/kg on a regimen in single or 2 to 4 divided daily doses.

The active substance can be utilized in a composition such as tablet, capsule, solution or suspension containing about 5 to about 500 mg per unit of dosage of a compound or mixture of compounds of formula I. They may be compounded in conventional manner with a physiologically acceptable vehicle or carrier, excipient, binder, preservative, stabilizer, flavor, etc. as called for by accepted pharmaceutical practice. Also as indicated in the discussion above, certain members additionally serve as intermediates for other members of the group.

The following examples represent preferred embodiments of the invention.

EXAMPLE 1

[1β,2α(5Z),3β,4β]-7-[3-[[(Propoxycarbonyl)hydrazono]methyl]-7-oxabicyclo[(2.2.1]hept-2-yl]-5-heptenoic acid

A. n-Propyl hydrazinocarboxylate

Hydrazine hydrate (1.9 g, 0.038 mmol) and di-n-propyl carbonate (5.3 g, 0.036 mmol) were heated at reflux for 43 hours. The reaction was filtered and the filtrate was concentrated in vacuo to leave a colorless oil (3.5 g, 0.029 mol, 82%).

B. [1β,2α(5Z),3β,4β]-7-[3-Formyl-7-oxabicyclo[2.2.1]hept-2-yl]-5-heptenoic acid, methyl ester A solution of pyridine (14.6 ml, 181 mmol) in dichloromethane (500 ml) was treated portionwise with chromium trioxide (9.06 g, 90.6 mmol) with vigorous stirring. After addition was complete, the mixture was stirred at room temperature for 30 minutes then treated with celite (30 g) then [1β,2α(5Z),3β,4β]-7-[3-(hydroxymethyl)-7-oxabicyclo[2.2.1]hept-2-yl]-5-heptenoic acid, methyl ester prepared as described in U.S. Pat. No. 4,143,054 (4.05 g, 15.1 mmoles) in dichloromethane (10 ml). The reaction mixture was stirred at room temperature for 20 minutes then filtered through celite. The filtrate was washed with 5% sodium bicarbonate (2×300 ml), 10% hydrochloric acid (2×300 ml) and again with 5% sodium bicarbonate (1×300 ml). The dichloromethane solution was dried over magnesium sulfate and concentrated in vacuo. The residue was dissolved in ether and filtered through a pad of Baker silica gel, washed with ether and the filtrate taken to dryness in vacuo leaving 3.7 g (92%) of pale yellow oil.

C. [1β,2α(5Z),3β,4β]-7-[3-[[(Propoxycarbonyl)hydrazono]methyl]-7-oxabicyclo[2.2.1]hept-2-yl]-5-heptenoic acid, methyl ester

[1β,2α(5Z),3β,4β]-7-[3-Formyl-7-oxabicyclo-[2.2.1]hept-2-yl]-5-heptenoic acid, methyl ester, prepared as described in Example 1, part B, (532 mg, 2 mmol) was dissolved in distilled ethanol (10 ml) in an argon atmosphere and the title A compound (260 mg, 2.2 mmol) was added. The mixture was stirred at room temperature 3 hours and then taken to dryness in vacuo. The oily residue was chromatographed on silica gel 60 (30 g), eluting with ether-pet ether 3:1 to give the title compound as a viscous oil (612 mg, 83.5%) TLC silica gel, Et$_2$O-P.E. 3:1, vanillin R$_f$=0.25. $^1$H NMR indicate this is the anti isomer.

D.

[1β,2α(5Z),3β,4β]-7-[3-[[(Propoxycarbonyl)hydrazono]methyl]-7-oxabicyclo[2.2.1]hept-2-yl]-5-heptenoic acid Title C compound (327 mg, 0.89 mmol) was dissolved in THF (40 ml) and water (7.8 ml) in an argon atmosphere. 1 N LiOH solution (8.9 ml) was added and the mixture was stirred at room temperature 5.5 hours. 1 N HCL (10.4 ml) was added to adjust pH to 3. The solution was poured into saturated NaCl solution (300 ml). The product was extracted into ethyl acetate (4×100 ml). The combined ethyl acetate extracts were washed with saturated NaCl solution (4×100 ml), dried over MgSO$_4$, filtered and freed of solvent in vacuo to give the title product (304 mg, 97%) as a viscous oil. TLC: silica gel, 5% MeOH in EtOAc, vanillin R$_f$=0.18. $^1$H and $^{13}$C NMR's indicate this is an anti isomer.

Anal. Calcd for C$_{18}$H$_{28}$O$_5$N$_2$: C, 61.35; H, 8.01; N, 7.95; Found: C, 61.41; H, 8.27; N, 7.79.

EXAMPLE 2

[1β,2α(5Z),3α,4β]-7-[3-[[(Propoxycarbonyl)hydrazono]methyl]-7-oxabicyclo[2.2.1]hept-2-yl]-5-heptenoic acid A. [1β,2α(5Z), 3α,4β]-7-[3-Formyl-7-oxabicyclo[2.2.1]hept-2-yl]-5-heptenoic acid, methyl ester A solution of pyridine (14.3 ml, 177 mmol) in dichloromethane (500 ml) was treated portionwise with chromium trioxide (8.9 g, 89 mmol) with vigorous stirring. After addition was complete, the mixture was stirred at room temperature for 30 minutes then treated with celite (30 g) then [1β,2α(5Z),3α,4β]-7-[3-(hydroxymethyl)-7-oxabicyclo[2.2.1]hept-2-yl]-5-heptenoic acid, methyl ester prepared as described in U.S. Pat. No. 4,143,054 (4 g, 14.96 mmoles) in dichloromethane (20 ml) was added dropwise over a 20 minute period. The reaction mixture was stirred at room temperature for 30 minutes then filtered through celite. The filtrate was washed with sat'd sodium bicarbonate soln (2×250 ml), 10% hydrochloric acid (2×100 ml), and again with sat'd sodium bicarbonate soln (1×250 ml). The dichloromethane solution was dried over magnesium sulfate and concentrated in vacuo. A brownish residue was dissolved in ether and passed through a pad of Baker silica gel, then eluted with more ether and the ether solution was taken to dryness in vacuo leaving 3.86 g near colorless oil.

B.

[1β,2α(5Z),3α,4β]-7-[3-[[(Propoxycarbonyl)hydrazono]methyl]-7-oxabicyclo[2.2.1]hept-2-yl]-5-heptenoic acid, methyl ester

[1β,2α(5Z),3α,4β]-7-[3-Formyl-7-oxabicyclo[2.2.1]hept-2-yl]-5-heptenoic acid, methyl ester, prepared as described in Example 2, part A, (532 mg, 2 mmol) and n-propyl hydrazinocarboxylate, prepared as described in Example 1, part A, (283.2 mg, 2.4 mmol) were dissolved in EtOH (10 ml) and the reaction was stirred for 2 hours at room temperature. The reaction was concentrated in vacuo leaving a colorless oil (672 mg), which was purified by silica gel column (silica 60, 30 g) eluted with Et$_2$O/pet ether (3.5/1.5) to give a colorless oil (599 mg, 1.63 mmol, 81%).

C.

[1β,2α(5Z),3α,4β]-7-[3-[[(Propoxycarbonyl)hydrazono]methyl]-7-oxabicyclo[2.2.1]hept-2-yl]-5-heptenoic acid 1 N-LiOH (6.7 ml) was added to title B ester (248 mg, 0.67 mmol) dissolved in THF (34 ml) and H$_2$O (6.7 ml) at room temperature. The reaction was stirred for 6 hours at room temperature. 1 N-HCL (6.7 ml) was added to the reaction, which was poured into brine (~50 ml). The products were extracted with EtOAc (100 ml×3). The combined EtOAc layers were washed with brine (50 ml×2), and dried over MgSO$_4$. Filtration and evaporation of solvents afforded a yellow oil (235 mg), which was purified by silica gel column (silicar CC-7, 25 g) eluted with CH$_2$Cl$_2$/MeOH (9.75/0.25) to give the title product as a colorless oil (226 mg, 0.64 mmol, 95%).

Anal. Calcd for C$_{18}$H$_{28}$N$_2$O$_5$: C, 61.32; H, 8.00; N, 7.97; Found: C, 61.15; H, 8.07; N, 8.02.

EXAMPLE 3

[1β,2α(5Z),3α,4β]-7-[3-[[(Propoxycarbonyl)methylhydrazono]methyl]-7-oxabicyclo[2.2.1]hept-2-yl]-5-heptenoic acid A. 1-Methyl-1-propoxycarbonyl hydrazine Methylhydrazine (7.2 g, 0.16 mole) and di-n-propylcarbonate (5 g, 0.034 mole) were stirred at room temperature for 96 hours to yield 1-methyl-1-propoxycarbonyl hydrazine and 2-methyl-1-propoxycarbonyl hydrazine in approximately equal amounts. The reaction was concentrated in vacuo and fractionated (F1, 2.0 g, 72°-76° a/0.8 mm Hg; F2, 1.1 g, 76°-88° a/0.8 mm Hg; F3, 1.1 g, 88°-90° a/0.8 mm Hg). F1 was a mixture of 1-methyl-1-propoxycarbonyl hydrazine and 2-methyl-1-propoxycarbonyl hydrazine in 4 to 1 ratio. F2 was an equal mixture of 1-methyl-1-propoxycarbonyl hydrazine and 2-methyl-1-propoxycarbonyl hydrazine. F3 was mostly 2-methyl-1-propoxycarbonyl hydrazine. Thus the yield of 1-methyl-1-propoxycarbonyl hydrazine was ca. 46%.

B.

[1β,2α(5Z),3α,4β]-7-[3-[[(Propoxycarbonyl)methylhydrazono]methyl]-7-oxabicyclo[2.2.1]hept-2-yl]-5-heptenoic acid, methyl ester A mixture of carbazate (1-methyl-1-propoxycarbonyl hydrazine and 2-methyl-1-propoxycarbonyl hydrazine) in a ratio of 1:1, (356 mg, 2.70 mmole) and [1β,2α(5Z),3α,4β]-7-[3-formyl-7-oxabicyclo[2.2.1]hept-2-yl]-5-heptenoic acid, methyl ester prepared as described in Example 2A, (360 mg, 1.35 mmole) in MeOH (5 ml) were stirred at room temperature for 17 hours. The reaction was concentrated in vacuo and the residue was purified by SiO$_2$ column (SiO$_2$, 40 g) eluted with pet ether/ether-½ to give a colorless oil (381.5 mg, 1.0 mmole, 74%).

C.
[1β,2α(5Z),3α,4β]-7-[3-[[(Propoxycarbonyl)methylhydrazono]methyl]-7-oxabicyclo[2.2.1]hept-2-yl]-5-heptenoic acid 1 N-LiOH (10 ml) was added to a magnetically stirred solution of the title B carbazone (381.5 mg, 1 mmole) in THF (50 ml) and H$_2$O (10 ml). Stirring was continued for 4.5 hours. 1 N HCl (10 ml) and solid NaCl were added until the water layer was saturated. Then the products were extracted with EtOAc (70 ml×2), which was washed with brine once, and dried over MgSO$_4$. Filtration and evaporation of solvent gave a pale yellow oil (366.7 mg) which was purified by SiO$_2$ column (silicar CC-7, 30 g) eluted with CH$_2$Cl/MeOH=9.8/0.2 to give the title product in the form of a colorless oil (285.3 mg, 0.78 mmole, 78%).

TLC: Silica gel, 5% MeOH in CH$_2$Cl$_2$; R$_f$=0.25, PMA.

Anal. Calcd for C$_{19}$H$_{30}$N$_2$O$_5$: C, 62.25; H, 8.24; N, 7.67; Found: C, 61.90; H, 8.21; N, 7.44.

EXAMPLE 4

[1β,2α(5Z),3β,4β]-7-[3-[[(Propoxycarbonyl)methylhydrazono]methyl]-7-oxabicyclo[2.2.1]hept-2-yl]-5-heptenoic acid Following the procedure of Example 1 except substituting 1-methyl-1-propoxycarbonyl hydrazine for n-propyl hydrazinocarboxylate, the title compound is obtained.

EXAMPLE 5

[1β,2α(5Z),3α,4β]-7-[3-[[(1-Oxopentyl)methylhydrazono]methyl]-7-oxabicyclo[2.2.1]hept-2-yl]-5-heptenoic acid Following the procedure of Example 2 except substituting 1-methyl-1-pentanoyl hydrazine (prepared by reacting valeryl chloride and methyl hydrazine) for n-propyl hydrazinocarboxylate, the title compound is obtained.

EXAMPLE 6

[1β,2α(5Z),3β,4β]-7-[3-[[(1-Oxopentyl)methylhydrazono]methyl]-7-oxabicyclo[2.2.1]hept-2-yl]-5-heptenoic acid

A.
[1β,2α(5Z),3β,4β]-7-[3-Formyl-7-oxabicyclo[2.2.1]hept-2-yl]-5-heptenoic acid, methyl ester The title aldehyde was prepared as described in Example 1, Part B.

B.
[1β,2α(5Z),3β,4β]-7-[3-[[(1-Oxopentyl)methylhydrazono]methyl]-7-oxabicyclo[2.2.1]hept-2-yl]-5-heptenoic acid, methyl ester A solution of the title A aldehyde (532 mg, 2 mmol) and 1-methyl-1-pentanoyl hydrazine, prepared as described in Example 5, (286 mg, 2.2 mmol) in EtOH (10 ml) is stirred at room temperature for 2 hours. The reaction mixture is poured into 100 ml of ether and washed with 1 N HCl (2×20 ml), saturated NaHCO$_3$ solution (2×20 ml) and saturated NaCl solution (2×20 ml). The ether solution is dried over MgSO$_4$, filtered and freed of solvent in vacuo leaving 748 mg (99%) of oil. This is chromatographed on 30 g silica gel 60, eluting with ether to give 529 mg (70%) of the title B compound as a viscous oil.

C.
[1β,2α(5Z),3β,4β]-7-[3-[[(1-Oxopentyl)methylhydrazono]methyl]-7-oxabicyclo[2.2.1]hept-2-yl]-5-heptenoic acid Title B compound (234 mg, 0.62 mmol) is dissolved in THF (30 ml) and water (5.8 mg). A solution of 1 N LiOH (6.2 ml) is added and the mixture is stirred at room temperature 4.5 hours. 1 N HCl (9 ml) is then added and the solution is poured into saturated NaCl solution (250 ml). The product is extracted into ethyl acetate (3×100 ml). The combined ethyl acetate extracts are washed with saturated NaCl solution (4×100 ml), dried over MgSO$_4$, filtered and freed of solvent in vacuo leaving 210 mg of glossy material. This is chromatographed on 18 g silica gel 60 eluting with 3% MeOH in CH$_2$Cl$_2$ to give clean title product as a viscous oil.

EXAMPLE 7

[1β,2α(5Z),3β,4β]-7-[3-[(Ethylbenzoylhydrazono)methyl]-7-oxabicyclo[2.2.1]hept-2-yl]-5-heptenoic acid

A.
[1β,2α(5Z),3β,4β]-7-[3-[(Ethylbenzoylhydrazono)methyl]-7-oxabicyclo[2.2.1]hept-2-yl]-5-heptenoic acid, methyl ester 1-Ethyl-1-benzoyl hydrazine (360 mg, 2.2 mmol) is added to a solution of [1β,2α(5Z),3β,4β]-7-[3-formyl-7-oxabicyclo[2.2.1]hept-2-yl]-5-heptenoic acid, methyl ester, prepared as described in Example 1, (532 mg, 2 mmol) in 10 ml dist EtOH in an argon atmosphere. The mixture is stirred at room temperature 2 hours and then poured into 100 ml ether. The ether solution is washed with 1 N HCl (2×20 ml), saturated NaHCO$_3$ solution (2×20 ml) and saturated NaCl solution (2×20 ml), dried over MgSO$_4$, filtered and freed of solvent in vacuo leaving 667 mg oil. This is chromatographed on 38 g silica gel 60, eluting with ether to give clean methyl ester as a viscous oil.

B.
[1β,2α(5Z),3β,4β]-7-[3-[(Ethylbenzoylhydrazono)methyl]-7-oxabicyclo[2.2.1]hept-2-yl]-5-heptenoic acid The methyl ester of Part A (284 mg, 0.69 mmol) is dissolved in 35 ml THF and 6.5 ml water in an argon atmosphere and 1 N LiOH solution (6.9 ml) was added. The mixture is stirred at room temperature 3½ hours and then 1 N HCl solution (13.8 ml) is added. The solution is poured into 250 ml saturated NaCl solution and the product is extracted into ethyl acetate (3×100 ml). The combined ethyl acetate extracts are washed with saturated NaCl solution (4×100 ml), dried over MgSO$_4$, filtered and freed of solvent in vacuo leaving 217 mg oil. This is chromatographed twice on silica gel 60. The first column is eluted with 5% MeOH in EtOAc and the second column is eluted with 3% MeOH in EtOAc to give the title product as a foam.

EXAMPLE 8

[1β,2α(5Z),3α,4β]-7-[3-(Ethylbenzoylhydrazono)methyl]-7-oxabicyclo[2.2.1]hept-2-yl]-5-heptenoic acid

A.

[1β,2α(5Z),3α,4β]-7-[3-[(Ethylbenzoylhydrazono)methyl]-7-oxabicyclo[2.2.1]hept-2-yl]-5-heptenoic acid, methyl ester 1-Ethyl-1-benzoyl hydrazine (328 mg) is added to [1β,2α(5Z),3α,4β]-7-[3-formyl-7-oxabicyclo[2.2.1]hept-2-yl]-5-heptenoic acid, methyl ester, prepared as described in Example 2, (532 mg, 2 mmol) dissolved in EtOH (10 ml) and a drop of AcOH and stirred overnight. The reaction is poured into Et₂O (150 ml), which is washed with 1 N HCl (30 ml×2), NaHCO₃ (saturated, 30 ml×2), brine (30 ml×2) and dried over MgSO₄. Filtration and evaporation of solvent in vacuo give a yellow oil (812 mg), which is purified by a silica gel column (SiO₂, 30 g) eluted with CH₂Cl₂/MeOH (9.5/0.5) to give the title A hydrazone (644 mg, 1.56 mmol, 78%).

B.

[1β,2α(5Z),3α,4β]-7-[3-[(Ethylbenzoylhydrazono)methyl]-7-oxabicyclo[2.2.1]hept-2-yl]-5-heptenoic acid The hydrazone from Part A (321 mg, 0.78 mmol) is dissolved in THF (40 ml) and H₂O (8 ml), and cooled to 0° C. 1 N LiOH (7.7 ml) is added. Stirring is continued at 0° C. for 4¼ hours. The reaction is quenched by addition of 10% oxalic acid to pH 3 and then poured into H₂O (200 ml). The products are extracted with EtOAc (150 ml×3) and the combined EtOAc layers are washed with H₂O (50 ml×3), brine (50 ml) and dried over MgSO₄. Filtration and evaporation of solvent in vacuo give a colorless oil (245 mg), which is purified by a silica column (silica 60, 25 g) eluted with CH₂Cl₂/MeOH (9.5/0.5) to give anti isomer of the title hydrazone.

EXAMPLE 9

[1β,2α(5Z),3β,4β]-7-[3-[[[(Phenylamino)carbonyl]methylhydrazono]methyl]-7-oxabicyclo[2.2.1]hept-2-yl]-5-heptenoic acid

A.

[1β,2α(5Z),3β,4β]-7-[3-[[[(Phenylamino)carbonyl]methylhydrazono]methyl]-7-oxabicyclo[2.2.1]hept-2-yl]-5-heptenoic acid, methyl ester

[1β,2α(5Z),3β,4β]-7-[3-Formyl-7-oxabicyclo[2.2.1]hept-2-yl]-5-heptenoic acid, methyl ester, prepared as described in Example 1, part B, (532 mg, 2 mmol) is dissolved in 10 ml dist. ethanol and treated with 2-methyl-4-phenyl semicarbazide (363 mg, 2.2 mmol) in an argon atmosphere. The mixture is stirred at room temperature 3 hours, then taken to dryness in vacuo. The residue is chromatographed on silica gel 60 (40 g), eluting with ether-pet ether (3:1) and ether to give the title anti isomer.

B.

[1β,2α(5Z),3β,4β]-7-[3-[[[(Phenylamino)carbonyl]methylhydrazono]methyl]-7-oxabicyclo[2.2.1]hept-2-yl]-5-heptenoic acid The title A anti isomer (338 mg, 0.82 mmol) is dissolved in THF (40 ml) and water (7.8 ml) in an argon atmosphere and treated with a 1 N LiOH solution (8.2 ml). The mixture is stirred at room temperature 6 hours and then acidified by adding 1 N HCl (9 ml) to bring the pH to ~3. The solution is poured into saturated NaCl solution (300 ml) and the product is extracted into ethyl acetate (4×100 ml). The combined EtOAc extracts are washed with saturated NaCl solution (4×100 ml), dried over MgSO₄, filtered and taken to dryness in vacuo leaving 281 mg (86%) of oil which starts to crystallize on standing. This is triturated with 4% MeOH in EtOAc. The white solid is harvested by filtration, washed with ethyl acetate and ether, then dried in vacuo to give the title product.

EXAMPLE 10

[1β,2α(5Z),3α,4β]-7-[3-[[[(Phenylamino)carbonyl]methylhydrazono]methyl]-7-oxabicyclo[2.2.1]hept-2-yl]-5-heptenoic acid

A.

[1β,2α(5Z),3α,4β]-7-[3-[[[(Phenylamino)carbonyl]methylhydrazono]methyl]-7-oxabicyclo[2.2.1]hept-2-yl]-5-heptenoic acid, methyl ester

[1β,2α(5Z),3α,4β]-7-[3-Formyl-7-oxabicyclo[2.2.1]hept-2-yl]-5-heptenoic acid, methyl ester, prepared as described in Example 2, (532 mg, 2 mmol) and 2-methyl-4-phenylsemicarbazide (363 mg, 2.2 mmol) are dissolved in EtOH (10 ml). The reaction is stirred for 24 hours at room temperature, and concentrated in vacuo to give an oil (910 mg), which is purified by SiO₂ column (silica 60, 30 g) eluted with Et₂O/pet. ether (3.5/1.5) to give semicarbazone A in the form of a colorless oil.

B.

[1β,2α(5Z),3α,4β]-7-[3-[[[(Phenylamino)carbonyl]methylhydrazono]methyl]-7-oxabicyclo[2.2.1]hept-2-yl]-5-heptenoic acid Title A semicarbazone (262 mg, 0.634 mmol) is dissolved in THF (31.7 ml) and H₂O (6.3 ml) at room temperature. 1 N LiOH (6.3 ml) is added. After 5 hours stirring at room temperature, the reaction is quenched by an addition of 1 N HCl (6.3 ml) and poured into brine (50 ml). The products are extracted with EtOAc (80 ml×3). The combined EtOAc layers are washed with brine and dried over MgSO₄. Filtration and evaporation of solvent give an oil (225 mg) which is purified by silica gel column (silicar CC-7) to give the title product in the form of a colorless oil.

EXAMPLE 11

[1β,2α(5Z),3α,4β]-7-[3-[[(3-Pyridinylcarbonyl)methylhydrazono]methyl]-7-oxabicyclo[2.2.1]hept-2-yl]-5-heptenoic acid

A.

[1β,2α(5Z),3α,4β]-7-[3-[[(Pyridinylcarbonyl)methylhydrazono]methyl]-7-oxabicyclo[2.2.1]hept-2-yl]-5-heptenoic acid, methyl ester

[1β,2α(5Z),3α,4β]-7-[3-Formyl-7-oxabicyclo[2.2.1]hept-2-yl]-5-heptenoic acid, methyl ester (532 mg, 2.0 mmol) is dissolved in ethanol (10 ml) in an argon atmosphere. 1-Methyl-1-nicotinoyl hydrazine (332 mg, 2.2 mmol) is added and the mixture is stirred at room temperature. At the end of 3 hours, more of the hydrazide (60 mg, 0.4 mmol) is added and stirred is continued for an additional 1.5 hours. The solvent is removed in vacuo and the residue is chromatographed on silica gel 60 (50 g) eluting with 2% MeOH in EtOAc to give the title A compound.

B.
[1β,2α(5Z),3α,4β]-7-[3-[[(3-Pyridinylcarbonyl)methylhydrazono]methyl]-7-oxoabicyclo[2.2.1]hept-2-yl]-5-heptenoic acid The title A methyl ester (391 mg, 0.98 mmol) is dissolved in THF (50 ml) and water (8.5 ml). 1 N LiOH solution (9.8 ml) is added and the mixture is stirred at room temperature 4 hours. 1 N HCl solution (9.8 ml) is then added (pH ~5) and the mixture is poured into 300 ml saturated NaCl solution. The product is extracted into ethyl acetate (4×100 ml). The ethyl acetate extracts are washed with saturated NaCl solution (4×100 ml), dried (MgSO$_4$) and freed of solvent in vacuo leaving the title product.

EXAMPLE 12

[1β,2α(5Z),3β,4β]-7-[3-[[(3-Pyridinylcarbonyl)methylhydrazono]methyl]-7-oxoabicyclo[2.2.1]hept-2-yl]-5-heptenoic acid Following the procedure of Example 11 except substituting for the aldehyde employed in Example 11 part A, [1β,2α(5Z),3β,4β]-7-[3-formyl-7-oxabicyclo[2.2.1]hept-2-yl]-5-heptenoic acid, methyl ester, the title compound is obtained.

EXAMPLE 13

[1β,2α(5Z),3β,4β]-7-[3-[[(Cyclohexylcarbonyl)methylhydrazono]methyl]-7-oxabicyclo[2.2.1]hept-2-yl]-5-heptenoic acid Following the procedure of Example 7, except substituting 1-methyl-1-cyclohexylcarbonyl hydrazine for methyl benzoyl hydrazine, the title compound is obtained.

EXAMPLE 14

[1β,2α(5Z),3α,4β]-7-[3-[[(Cyclohexylcarbonyl)methylhydrazono]methyl]-7-oxabicyclo[2.2.1]hept-2-yl]-5-heptenoic acid Following the procedure of Example 8 except substituting 1-methyl-1-cyclohexylcarbonyl hydrazine for 1-methyl-1-benzoyl hydrazine, the title compound is obtained.

EXAMPLE 15

[1β,2α(5Z),3α,4β]-7-[3-[[(2-Oxo-1-piperidinyl)imino]methyl]-7-oxabicyclo[2.2.1]hept-2-yl]-5-heptenoic acid

A. 1-Amino-2-piperidone

Methyl δ-bromovalerate (9.75 g) in dry MeOH (50 ml) was added dropwise to a magnetically stirred solution of hydrazine hydrate (2.5 g) in dry MeOH (125 ml) over 40 minutes at room temperature. After 22 hours stirring at room temperature, an additional hydrazine hydrate (2.5 g) was added. Stirring was continued for 6 hours at room temperature. Then, sodium methoxide (sodium, 1.15 g) in dry MeOh (25 ml) was added dropwise to the reaction at room temperature, which was stirred overnight. Solvent was removed in vacuo and the residual sludge was distilled to give a desired compound, a colorless liquid (3.4 g, b.p. 84° C./0.4 mmHg)

B.
[1β,2α(5Z),3α,4β]-7-[3-[[(2-Oxo-1-piperidinyl)imino]methyl]-7-oxabicyclo-5-heptenoic[2.2.1]hept-2-yl]acid, methyl ester

[1β,2α(5Z),3α,4β]-7-[3-Formyl-7-oxabicyclo[2.2.1]hept-2-yl]-5-heptenoic acid, methyl ester, prepared as described in Example 2, Part A (532 mg), and 1-amino-2-piperidone (230 mg) in MeOH (10 ml) were stirred at room temperature overnight. Solvent was removed in vacuo and the residual oil was purified by SiO$_2$ column (silica 60, 30 g) eluted with pet. ether/ether (½) to give the desired title hydrazone (615.3 mg).

C.
[1β,2α(5Z),3α,4β]-7-[3-[[(2-Oxo-1-piperidinyl)imino]methyl]-7-oxabicyclo[2.2.1]hept-2-yl]-5-heptenoic acid 1 N LiOH (6.7 ml) was added to title B ester (248 mg, 0.67 mmol) dissolved in THF (34 ml) and H$_2$O (6.7 ml) at room temperature. The reaction was stirred for 6 hours at room temperature. 1 N HCl (6.7 ml) was added to the reaction, which was poured into brine (~50 ml). The products were extracted with EtOAc (100 ml×3). The combined EtOAc layers were washed with brine (50 ml×2), and dried over MgSO$_4$. Filtration and evaporation of solvents afforded a yellow oil (235 mg), which was purified by silica gel column (silicar CC-7, 25 g) eluted with CH$_2$Cl$_2$/MeOH (9/1) to give the title product as a colorless oil.

EXAMPLE 16

[1β,2α(5Z),3β,4β]-7-[3-[[(2-Oxo-1-piperidinyl)imino]methyl]-7-oxabicyclo[2.2.1]hept-2-yl]-5-heptenoic acid Following the procedure of Example 1, except substituting 1-amino-2-piperidone (prepared by reaction of hydrazine hydrate and methyl 5-bromopentanoate) for the Example 1A hydrazine, the title compound is obtained.

EXAMPLE 17

[1β,2α(5Z),3α,4β]-7-[3-[[(Phenoxycarbonyl)methylhydrazono]methyl]-7-oxabicyclo[2.2.1]hept-2-yl]-5-heptenoic acid

A.
[1β,2α(5Z),3α,4β]-7-[3-Formyl-7-oxabicyclo[2.2.1]hept-2-yl]-5-heptenoic acid

[1β,2α(5Z),3α,4β]-7-(3-Hydroxymethyl)-7-oxabicyclo[2.2.1]hept-2-yl]-5-heptenoic acid, methyl ester prepared as described in U.S. Pat. No. 4,143,054 is subjected to hydrolysis by reacting same with sodium hydroxide in the presence of methanol to form the title A acid.

The above hydroxymethyl compound is then oxidized by reaction with chromium trioxide employing the procedure set out in Example 1, Part B, to form the title aldehyde.

B.
[1β,2α(5Z),3α,4β]-7-[3-[[(Phenoxycarbonyl)methylhydrazono]methyl]-7-oxabicyclo[2.2.1]hept-2-yl]-5-heptenoic acid Following the procedure of Example 2, except substituting the 1-methyl-1-phenoxycarbonyl hydrazine for the n-propyl hydrazonocarboxylate, the title compound is obtained.

EXAMPLE 18

[1β,2α(5Z),3β,4β]-7-[3-[[(Phenoxycarbonyl)methylhydrazono]methyl]-7-oxabicyclo[2.2.1]hept-2-yl]-5-heptenoic acid Following the procedure of Example 17, except substituting [1β,2α(5Z),3β,4β]-7-[3-(hydroxymethyl)-7-oxabicyclo[2.2.1]hept-2-yl]-5-heptenoic acid, methyl ester for the methyl ester employed in Example 17, Part A, the title compound is obtained.

EXAMPLE 19

[1β,2α(5Z),3β,4β]-7-[3-[[(1-Oxohexyl)methyl]hydrazono]methyl]-7-oxabicyclo[2.2.1]hept-2-yl]-5-heptenoic acid Following the procedure of Example 5 except substituting 1-hexanoyl-1-methyl hydrazine for 1-pentanoyl-1-methyl hydrazine, the title compound is obtained.

EXAMPLE 20

[1β,2α(5Z),3α,4β]-7-[3-[[(1-Oxohexyl)methylhydrazono]methyl]-7-oxabicyclo[2.2.1]hept-2-yl]-5-heptenoic acid Following the procedure of Example 6 except substituting 1-hexanoyl-1-methyl hydrazine for 1-pentanoyl-1-methyl hydrazine, the title compound is obtained.

EXAMPLE 21

[1β,2α(5Z),3α,4β]-7-[3-[[[(n-Butylamino)carbonyl]ethylhydrazono]methyl]-7-oxabicyclo[2.2.1]hept-2-yl]-5-heptenoic acid Following the procedure of Example 10 except substituting 2-ethyl-4-butylsemicarbazide for 2-methyl 4-phenylsemicarbazide, the title compound is obtained.

EXAMPLE 22

[1β,2β,3α,4β]-7-[3-[[(1-Oxopentyl)methylhydrazino]methyl]-7-oxabicyclo[2.2.1]hept-2-yl]heptanoic acid A.
[1β,2β,3β,4β]-7-[3-(Hydroxymethyl)-7-oxabicyclo[2.2.1]hept-2-yl]-heptanoic acid, methyl ester To 800 mg (3.0 mmole) of the [1β,2β(5Z)3β,4β]-7-[3-(hydroxymethyl)-7-oxabicyclo[2.2.1]hept-2-yl]-5-heptenoic acid, methyl ester as prepared in U.S. Pat. No. 4,143,054, dissolved in 120 ml of ethyl acetate was added, under an argon atmosphere, 120 mg of 5% Pd on carbon. The argon atmosphere was exchanged for a slight positive pressure of hydrogen and the reaction was stirred for 8 hours at 25°, filtered through a celite plug and evaporated to provide 730 mg (90%) of the title A compound.

B.
[(1β,2β,3ξ,4β)]-7-[3-Formyl-7-oxabicyclo[2.2.1]hept-2-yl]heptanoic acid, methyl ester To 1.21 g (5.6 mmole, 2.0 equiv.) of pyridinium chlorochromate (PCC) and 20 ml of anhydrous $CH_2Cl_2$ was added, under an argon atmosphere, 730 mg (2.8 mmole) of the title A alcohol in 2 ml of $CH_2Cl_2$. The reaction was stirred for 2 hours at 25°, diluted with 100 ml of ether, filtered through a pad of florisil, and evaporated to furnish 670 mg (88%) of the title B compound as a white crystalline solid.

C.
[1β,2β,3α,4β]-7-[3-Formyl-7-oxabicyclo[2.2.1]hept-2-yl]heptanoic acid, methyl ester To 800.0 mg of the title B aldehyde in 20 ml of anhydrous methanol under an argon atmosphere at 25° was added 100 mg of sodium methoxide. The reaction was stirred for 2 hours, diluted with 100 ml of saturated ammonium chloride and extracted with four 100 ml portions of ether. The ethereal layer was washed with 50 ml of brine, dried over anhydrous magnesium sulfate and concentrated to afford 765.0 mg (98%) of the title C aldehyde.

D.
[(1β,2β,3α,4β)]-7-[3-[[(1-Oxopentyl)methylhydrazono]methyl]-7-oxabicyclo[2.2.1]hept-2-yl]heptanoic acid Following the procedure of Example 1, except substituting the above Part C aldehyde for the Example 1B aldehyde, the title product is obtained.

EXAMPLE 23

[1β,2β,3α,4β]-7-[3-[[(Propoxycarbonyl)methylhydrazono]methyl]-7-oxabicyclo[2.2.1]hept-2-yl]heptanoic acid Following the procedure of Example 22, except substituting 1-methyl-1-propoxycarbonyl hydrazne for the Example 1A carbazate, the title compound is produced.

EXAMPLE 24

[1β,2β,3α,4β]-7-[3-[(Ethylbenzoylhydrazono)methyl]-7-oxabicyclo[2.2.1]hept-2-yl]heptanoic acid Following the procedure of Example 22, excpt substituting 1-methyl-1-benzoyl hydrazine for the Example 5 hydrazide, the title compound is obtained.

EXAMPLE 25

[1β,2β,3α,4β]-7-[3-[[[(Phenylamino)carbonyl]methylhydrazono]methyl]-7-oxabicyclo[2.2.1]hept-2-yl]heptanoic acid Following the procedure of Example 22, except substituting 2-methyl-4-phenyl semicarbazide for the Example 1A carbazate, the title compound is produced.

EXAMPLE 26

[1β,2β,3α,4β]-7-[3-[[(3-Pyridinylcarbonyl)methylhydrazono]methyl]-7-oxabicyclo[2.2.1]hept-2-yl]heptanoic acid Following the procedure of Example 22, except substituting 1-methyl-1-nictotinoyl hydrazine for the Example 1A carbazate, the title compound is produced.

EXAMPLE 27

[1β,2β,3α,4β]-7-[3-[[(Cyclohexylcarbonyl)methylhydrazono]methyl]-7-oxabicyclo[2.2.1]hept-2-yl]heptanoic acid Following the procedure of Example 22, except substituting 1-methyl-1-cyclohexylcarbonyl hydrazine for the Example 1A carbazate, the title compound is obtained.

EXAMPLE 28

[1β,2β,3α,4β]-7-[3-[[(n-Butylamino)carbonyl]ethylhydrazono]methyl]-7-oxabicyclo[2.2.1]hept-2-yl]heptanoic acid Following the procedure of Example 22, except substituting 2-ethyl-4-n-butylsemicarbazide for 2-methyl-4-phenyl-semicarbazide, the title compound is obtained.

EXAMPLE 29

[1β,2β,3α,4β]-7-[3-[[(1-Oxopentyl)methylhydrazono]-methyl]-7-oxabicyclo[2.2.1]hept-2-yl]heptanoic acid Following the procedure of Example 22, except substituting 1-methyl-1-pentanoyl hydrazine for the Example 1A carbazate the title compound is obtained.

EXAMPLE 30

[1β,2β,3α,4β]-7-[3-[[1-(2-Oxo-1-piperidinyl)imino]methyl]-7-oxabicyclo[2.2.1]hept-2-yl]heptanoic acid Following the procedure of Example 22, except substituting 1-amino-2-piperidone for the Example 1A carbazate, the title compound is obtained.

EXAMPLE 31

[1β,2β,3α,4β]-7-[3-[[(Phenoxycarbonyl)methylhydrazono]methyl]-7-oxabicyclo[2.2.1]hept-2-yl]heptanoic acid Following the procedure of Example 22, except substituting 1-methyl-1-phenoxycarbonyl hydrazine for the Example 1A carbazate, and substituting [1β,2β(5Z),3ξ,4β]-7-[3-hydroxymethyl)-7-oxabicyclo[2.2.1]hept-2-yl]-5-heptenoic acid for the corresponding methyl ester, the title compound is obtained.

What is claimed is:

1. A compound having the structural formula

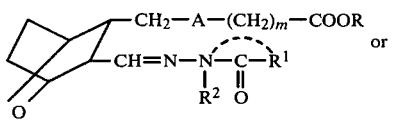

or

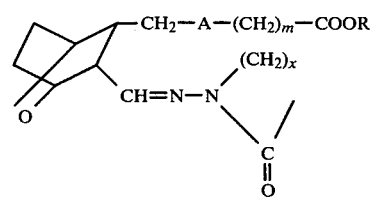

and including all stereoisomers thereof wherein
A is CH=CH or (CH₂)₂;
m is 1 to 8;
R is H or lower alkyl; R² is H or lower alkyl; and
R¹ is lower alkoxy and x is 3, 4 or 5.

2. The compound as defined in claim 1 having the formula

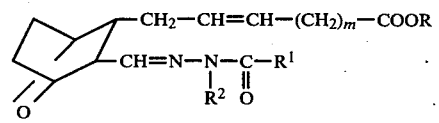

wherein R¹ is lower alkoxy including all stereoisomers thereof.

3. The compound as defined in claim 1 having the formula

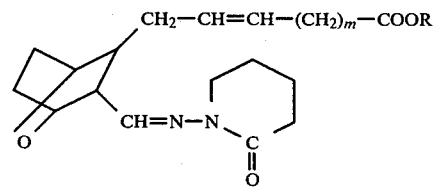

4. The compound as defined in claim 1 having the formula

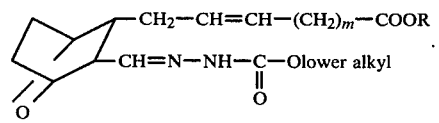

5. The compound as defined in claim 1 wherein A—(CH₂)ₘ—COOR is —CH=CH—(CH₂)₃—COOH.

6. The compound as defined in claim 1 having the name [1β,2α(5Z),3β,4β]-7-[3-[[(propoxycarbonyl)hydrazono]methyl]-7-oxabicyclo[2.2.1]hept-2-yl]-5-heptenoic acid or [1β,2α(5Z),3α,4β]-7-[3-[[(propoxycarbonyl)hydrazono]methyl]-7-oxabicyclo[2.2.1]hept-2-yl]-5-heptenoic acid or methyl esters of each, or stereoisomers thereof.

7. The compound as defined in claim 1 having the name [1β,2α(5Z),3α,4β]-7-[3-[[(propoxycarbonyl)methylhydrazono]methyl]-7-oxabicyclo[2.2.1]hept-2-yl]-5-heptenoic acid or its methyl ester of stereoisomers thereof.

8. The compound as defined in claim 1 having the name [1β,2α(5Z),3α,4β]-7-[3-[[(2-oxo-1-piperidinyl)imino]methyl]-7-oxabicyclo[2.2.1]hept-2-yl]-5-heptenoic acid, its methyl ester, or stereoisomers thereof.

9. A method of inhibiting platelet aggregation and bronchoconstriction, which comprises administering to the circulatory system of a mammalian host an effective amount of a compound as defined in claim 1 or a pharmaceutically acceptable salt thereof.

10. The method as defined in claim 9 wherein said compound is administered in an amount within the range of from about 1 to about 100 mg/kg.

11. A composition for inhibiting platelet aggregation and bronchoconstriction comprising an effective amount of a compound as defined in claim 1 or a pharmaceutically acceptable salt thereof, and a pharmaceutically acceptable carrier therefor.

12. A method of inhibiting platelet aggregation, which comprises administering to a mammalian host an effective amount of a compound as defined in claim 1 or a pharmaceutically acceptable salt thereof.

13. A method of inhibiting bronchoconstriction associated with asthma, which comprises administering to a mammalian host an effective amount of a compound as defined in claim 1 or a pharmaceutically acceptable salt thereof.

* * * * *

UNITED STATES PATENT AND TRADEMARK OFFICE
CERTIFICATE OF CORRECTION

PATENT NO. : 4,418,076
DATED : November 29, 1983
INVENTOR(S) : Masami Nakane et al.

It is certified that error appears in the above—identified patent and that said Letters Patent is hereby corrected as shown below:

On the abstract page, next to the structure, insert --I--.
On the abstract page, first line after the structure, delete "pa".
Column 12, line 64, "stirred" should read --stirring--.
Column 13, line 64, "MeOh" should read --MeOH--.
Column 14, line 3 should read --methyl]-7-oxabicyclo[2.2.1]-hept-2-yl]-5-heptenoic acid--.
Column 16, line 31, "hydrazne" should read --hydrazine--.

Signed and Sealed this

Twenty-second Day of May 1984

[SEAL]

Attest:

GERALD J. MOSSINGHOFF

Attesting Officer

Commissioner of Patents and Trademarks